United States Patent
Park

(10) Patent No.: US 12,161,138 B2
(45) Date of Patent: Dec. 10, 2024

(54) METHOD FOR PREPARATION OF NITRITE ION-CONTAINING ALLIUM TUBEROSUM FERMENTATE AND COMPOSITION THEREOF

(71) Applicant: Medience Co., Ltd., Chuncheon-si (KR)

(72) Inventor: Sang Jae Park, Yongin-si (KR)

(73) Assignee: Medience Co., Ltd., Chuncheon-si (KR)

( * ) Notice: Subject to any disclaimer, the term of this patent is extended or adjusted under 35 U.S.C. 154(b) by 884 days.

(21) Appl. No.: 17/258,933

(22) PCT Filed: Oct. 11, 2018

(86) PCT No.: PCT/KR2018/011960
§ 371 (c)(1),
(2) Date: Jan. 8, 2021

(87) PCT Pub. No.: WO2020/013388
PCT Pub. Date: Jan. 16, 2020

(65) Prior Publication Data
US 2021/0321643 A1   Oct. 21, 2021

(30) Foreign Application Priority Data

Jul. 10, 2018   (KR) ......................... 10-2018-0079769

(51) Int. Cl.
*A23L 19/00*   (2016.01)
*A23L 2/38*   (2021.01)
(Continued)

(52) U.S. Cl.
CPC ................. *A23L 2/382* (2013.01); *A23L 5/43* (2016.08); *A23L 19/00* (2016.08); *A61K 33/02* (2013.01);
(Continued)

(58) Field of Classification Search
CPC . A23L 2/382; A23L 5/43; A23L 19/00; A23L 19/03; A23L 33/105; A61K 33/02;
(Continued)

(56) References Cited

U.S. PATENT DOCUMENTS

2015/0245645 A1* 9/2015 Raskin ................ A21D 10/005
                                                                  426/640

FOREIGN PATENT DOCUMENTS

CN   103829224 A     6/2014
CN   104543896 A *   4/2015  ............. A23L 19/20
(Continued)

OTHER PUBLICATIONS

Chung et al., "Survey of nitrate and nitrite contents of vegetables grown in Korea", Food Additives and Contaminants, Jul. 2003, vol. 20, No. 7, 621-628 (Year: 2003).*

(Continued)

*Primary Examiner* — Elizabeth Gwartney
*Assistant Examiner* — Andrew E Merriam
(74) *Attorney, Agent, or Firm* — Sughrue Mion, PLLC

(57) ABSTRACT

The present invention relates to a method for preparation of a fermented *Allium tuberosum* composition which is obtained by inoculating and fermenting *Allium tuberosum* with yeast to generate nitrite ions and adding an anthocyanin to stabilize the nitrite ions, and to the fermented *Allium tuberosum* composition, whereby when ingested into the body, the natural nitrite ions are converted into nitric oxide to induce various biological activities such as hypotension, immunopotentiation, improved blood circulation, and the like. An anthocyanin can be obtained in the form of an extract from aronia, purple corn, black rice, berries such as blueberries and so forth, black bean, and the like and can improve the thermal stability of nitrite ions. Provided are thus a method for preparing a nitrite ion-stabilized, fer- (Continued)

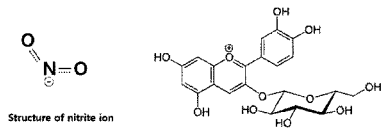

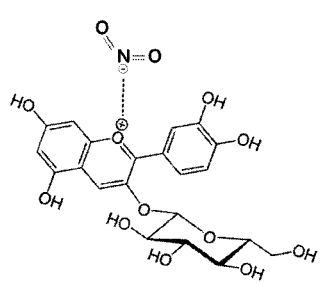

Schematic view of ionic bond between anthocyanin and nitrite ion mented *Allium tuberosum* liquid by adding an anthocyanin to a fermented *Allium tuberosum* liquid and a composition thereof.

1 Claim, 1 Drawing Sheet

(51) Int. Cl.
A23L 5/43 (2016.01)
A61K 33/02 (2006.01)
A61K 36/064 (2006.01)
A61K 36/8962 (2006.01)
A61K 47/54 (2017.01)

(52) U.S. Cl.
CPC ........ *A61K 36/064* (2013.01); *A61K 36/8962* (2013.01); *A61K 47/549* (2017.08); *A23V 2002/00* (2013.01); *A61K 2236/19* (2013.01)

(58) Field of Classification Search
CPC .............. A61K 36/064; A61K 36/8962; A61K 2236/19
See application file for complete search history.

(56) References Cited

FOREIGN PATENT DOCUMENTS

| CN | 106213248 A | * | 12/2016 |
| JP | 2006-298871 A | | 11/2006 |
| KR | 10-2009-0032547 A | | 4/2009 |
| KR | 10-0891608 B1 | | 4/2009 |
| KR | 10-2014-0056802 A | | 5/2014 |
| KR | 10-2015-0031712 A | | 3/2015 |
| KR | 10-2015-0043585 A | | 4/2015 |
| KR | 10-1608502 B1 | | 4/2016 |
| KR | 10-2016-0117029 A | | 10/2016 |
| KR | 10-2017-0097889 A | | 8/2017 |
| KR | 10-1794637 B1 | | 11/2017 |
| KR | 10-2018-0031438 A | | 3/2018 |
| KR | 10-1935538 B1 | | 1/2019 |

OTHER PUBLICATIONS

CN-103829224-A ( (Machine translation from Clarivate) (Year: 2014).*
CN-104543896-A 9Machine translation from Clarivate) (Year: 2015).*
CN-106213248-A (Machine translation from Clarivate) (Year: 2016).*
Carlos Andres Galan-Vidal, "Determination of Nitrites in Commercial Sausages by Anthocyanins Degradation. Experimental Design and Optimization", J. Mex. Chem. Soc., 2014, pp. 180-184, vol. 58, No. 2.
International Search Report for PCT/KR2018/011960 dated, Apr. 8, 2019 (PCT/ISA/210).

* cited by examiner

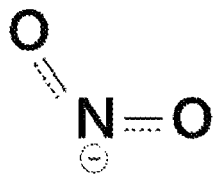
Structure of nitrite ion
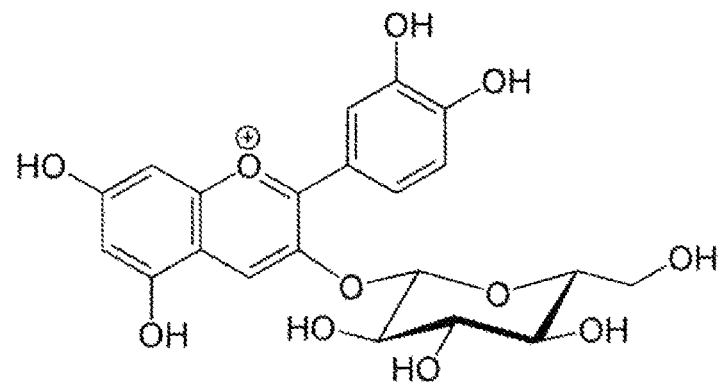
Structure of anthocyanin(C3G)
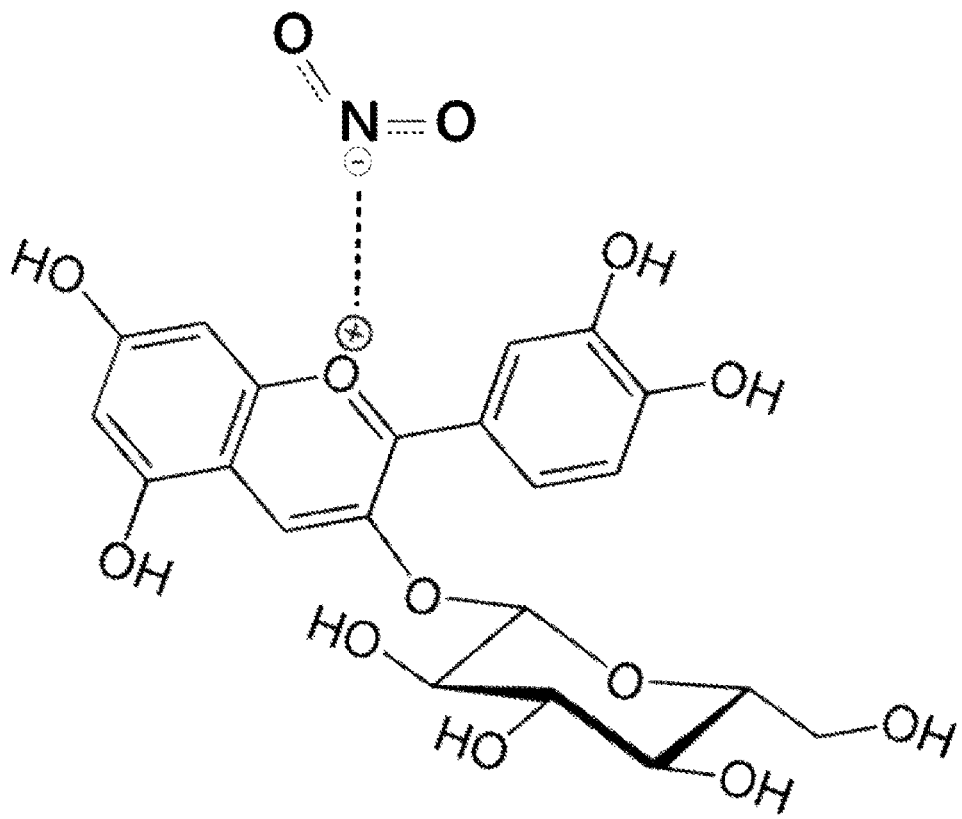
Schematic view of ionic bond between anthocyanin and nitrite ion

METHOD FOR PREPARATION OF NITRITE ION-CONTAINING ALLIUM TUBEROSUM FERMENTATE AND COMPOSITION THEREOF

CROSS REFERENCE TO RELATED APPLICATIONS

This application is a National Stage of International Application No. PCT/KR2018/011960 filed Oct. 11, 2018, claiming priority based on Korean Patent Application No. 10-2018-0079769 filed Jul. 10, 2018, the entire disclosures of which are incorporated by reference herein.

TECHNICAL FIELD

The present invention relates to a fermentation method for increasing the production of nitrite ions based on the enzyme component contained in *Allium tuberosum* and the cultured yeast by inoculating and culturing yeast in *Allium tuberosum*, and to a food composition for stabilizing the same.

BACKGROUND ART

It is generally known that plants contain a large number of nitrate ions, which are components of fertilizers absorbed from the roots thereof. In addition, nitrate ions are reduced to nitrite ions, which are used to synthesize proteins in plants, by the action of nitrate reductase to synthesize proteins in plants. These nitrate ions of plants are reduced to nitrite in the process of human consumption of plants through vegetables. Nitrite is absorbed by the human body and is converted to nitric oxide to exhibit various physiological activities in the human body. Therefore, when the nitrate ions in plants can be converted into nitrite ions within as a short time as possible and ingested in the human body, the concentration of nitric oxide can be increased and thus beneficial physiological activities such as immunity enhancement and blood flow improvement can be obtained.

Therefore, in the present invention, a method for inoculating and fermenting yeast having a reductase enzyme, in particular, using edible vegetables was developed and nitrate ions were converted to nitrite ions by reduction. A purple corn extract containing anthocyanin cations as counter ions to the nitrate (nitrite) ions was added to stabilize the nitrate (nitrite) ions, to maintain a stable concentration without being lost at high temperatures, and thereby to reduce the nitrite to nitric oxide in the body when ingested. As a result, a food composition that exhibits various physiological activities can be obtained.

DISCLOSURE

Technical Problem

Nitric oxide is known to have various physiological activities such as lowering blood pressure due to vasodilation, enhancing immunity, and improving blood flow in the human body. However, it is difficult to increase nitric oxide by a conventional method. In the present invention, to obtain various physiological activities by increasing nitric oxide, an attempt was made to develop a vegetable fermented product with an increased concentration of nitrite ions, which are a precursor to nitric oxide. Thus, it is an object of the present invention to obtain a fermented product having stability by solving the problem in which nitrate ions or nitrite ions are lost when heat-sterilized in a liquid state and thereby acquire a vegetable fermented product with a high concentration of nitrite ions.

Technical Solution

For the production of fermented vegetable products with an increased concentration of nitrite ions, *Allium tuberosum* was selected as a vegetable that has the highest nitrate ion content, can be stably supplied as a raw material, and can be supplied in great amounts, based on the results of analysis of the concentration of nitrate ions contained in vegetables. *Bacillus*, yeast and the like are tested as strains that convert nitrate ions into nitrite ions to select an active strain, and the conditions for maximizing the generation of nitrite ions are determined for strains found to have efficacy. A purple corn extract containing anthocyanin cations as counter ions to the nitrite ions was added, to stabilize the nitrite ions, and thereby to maintain a high concentration without loss of nitrite ions even upon sterilization to obtain products. As a result, the present invention has been completed by accomplishing the object of the present invention.

Advantageous Effects

The present invention relates to a method for producing a fermented product containing stabilized nitrite ions using vegetables, in particular, using *Allium tuberosum*. Nitrite ions are produced by fermentation, the nitrite ions are converted to nitric oxide in vivo when ingested in the form of a fermented beverage, and various and very useful physiological activities such as lowering blood pressure due to vasodilation, enhancing immunity, and improving blood flow can be obtained. The fermented product can be easily used as a liquid functional beverage or a health functional food produced by powderization.

BRIEF DESCRIPTION OF DRAWINGS

FIG. 1 shows the chemical structures and ionic bonding of nitrite, nitrate and anthocyanin.

BEST MODE

Hereinafter, detailed technical features constituting the present invention will be described in detail as follows. However, in the process of describing the present invention, a detailed description will be omitted for features that are determined to be issues that can be recognized as common basic matters in the related field.

According to the present invention, the popular edible *Allium tuberosum* is inoculated with the self-selected strain, *Saccharomyces cerevisiae* MD315, and the result is cultured under aerobic conditions, to convert the nitrate ions contained in the *Allium tuberosum* into nitrite ions, a purple corn extract containing anthocyanin is added thereto to stabilize the nitrate ions based on ionic bonding and finally obtain a fermented *Allium tuberosum* composition containing stabilized nitrite ions.

*Allium tuberosum* is known to contain vitamins A, B1, B2, C and the like and minerals such as calcium and iron. *Allium tuberosum* is known to have intestinal functions to make blood clear, have an effect of enhancing appetite, and have anti-inflammatory, antibacterial and antipyretic effects. The unique scent of *Allium tuberosum* is also known to calm the nerves. In addition, *Allium tuberosum* can strengthen liver functions and can be helpful for cold body or cold lower abdomen. The sulfur component contained in *Allium tuberosum* has fatigue recovery, nutritional and tonic effects, and the fiber of *Allium tuberosum* is effective for treating constipation, and *Allium tuberosum* contains beta-carotene effective in removing reactive oxygen species and preventing aging.

In general, nitrite ions are converted into nitric oxide in the body when ingested orally, thereby improving various and essential physiological activities such as vasodilation, improvement of blood circulation, hair growth, improvement of gastrointestinal motility, antioxidant activity, amelioration of impotence, lowering blood pressure, and anti-diabetes. The converted nitric oxide acts as a signal transducer in blood vessels for several seconds, then decomposes and disappears. Nitric oxide, which is a bioactive substance that was discovered by Dr. Louis Ignarro, who was awarded the Nobel Prize in Physiological Medicine therefor, can be an essential substance for restoring health by solving side effects caused by chronic diseases such as blood pressure-associated disorders.

In the present invention, in an attempt to utilize the physiological activity of nitric oxide, the production of nitrite ions by natural fermentation was studied, and in order to maximize the conversion to nitrite ions, *Saccharomyces cerevisiae* MD315, the yeast strain whose activity was identified, was selected and conditions for producing as many nitrite ions as possible were determined by establishing an optimized fermentation process. *Allium tuberosum* was washed and sliced, water was added thereto in an amount of 3 to 10 times the weight of the *Allium tuberosum* and then sterilized, and the selected yeast strain, MD315, was inoculated thereinto, and cultured at 30 to 35 degrees Celsius for 2 to 4 days, most preferably, for 3 days while bubbling air for aerobic conditions, to conduct fermentation for production of nitrite ions. When fermentation is completed, a fermentation broth containing 100 to 1,000 ppm of nitrite ions is obtained and the *Allium tuberosum* leaf is removed by filtration to obtain a liquid fermentation product. As a result of analysis of the liquid fermentation product, an extract containing anthocyanin as a stabilizer for stabilizing the content of nitrite ions was added, followed by mixing. As a result, anionic nitrite forms an ionic bond with cationic anthocyanin, thus providing the effect of minimizing the loss of nitrite ions in the subsequent concentration and sterilization process, and obtaining physiological activities such as antioxidant activity and improved liver function of anthocyanin added thereto.

Most preferably, the process of inoculating and fermenting the MD315 strain was conducted for 3 days. When the process was conducted for a time longer than 3 days, the amount of nitrite ions produced decreased.

The fermented *Allium tuberosum* solution containing nitrite may be lost during high-temperature sterilization. The cationic anthocyanin introduced to prevent this problem is preferably added at a weight ratio of 1:0.001 to 1:2.0, most preferably, 1:0.05 to 1:0.5, based on the amount of nitrite ions since the anthocyanin cations may form ionic bonds with nitrate ions or nitrite ions. The anthocyanin added as a raw material is most preferably an extract containing C3G (cyanidin-3-glucoside, molecular weight 449) or a purified product thereof. Representative examples thereof include a *Rubus coreanus* Miguel extract, a purple corn extract, an aronia extract, a blueberry extract, a mulberry extract, a *Schisandra chinensis* extract, a blackcurrant extract, a bilberry extract, a blackberry extract, a purple sweet potato extract, a beetroot extract, and purified products of these extracts, and a purple pigment as a natural colorant and food additive. Most preferred is the use of a purple corn extract. In the case of an extract containing 2% (w/w) anthocyanin, anthocyanin may be added at a weight ratio of 1:0.05 to 1:50 of the nitrite ions ($NO_2^-$, molecular weight: 46) to the anthocyanin. When the weight ratio of nitrite to anthocyanin in the amount of the extract added for stabilization is lower than 1:0.001, the stabilization effect may be significantly reduced, and when the weight ratio is greater than 1:2.0, economic efficiency is reduced due to the addition of an amount excessively greater than the required amount. At the same time, reduction of nitrite ions may be caused by heating, thus resulting in decrease in nitrite ions.

The fermented *Allium tuberosum* solution, to which anthocyanin is added, is concentrated and sterilized by a low-temperature vacuum drying process to obtain a fermented *Allium tuberosum* composition in a stabilized state and containing a high content of nitrite ions.

Anthocyanin is added to the fermented *Allium tuberosum* solution, and plays a crucial role in maintaining stably nitrite ions, without decomposition even under sterilization conditions, as shown in Table 1 below.

In general, there are a variety of anthocyanins such as cyanin, pelargonin, peonidin, delphinidin, petunidin, malvidin and the like. The anthocyanins mentioned in the present invention are not affected by the presence or absence of binding of sugar in consideration of the corresponding mechanism of action, so anthocyanins and anthocyanidins are targeted. The reason for this is that the bond of the present invention is an ionic bond and thus the presence or absence of sugar bonding does not affect the charge configuration of anthocyanins, so that a stabilizing effect can be obtained through ionic bonding, regardless of whether or not sugar bonding is present. Therefore, even if sugar is removed from the extract containing anthocyanin by enzymatic treatment or fermentation, the stabilizing effect by ionic bonding of the present invention is applied based on the same technical idea.

TABLE 1

Changes in content of nitrite ions depending on sterilization conditions after addition of purple corn extract (containing 2% anthocyanin) (proportion of nitrite ions remaining after sterilization (%))

| | Nitrite:purple corn extract = 1:0.3 | Nitrite:purple corn extract = 1:0.0 (in the case of non-addition) |
| --- | --- | --- |
| 60° C., 1 hour | 99 | 75 |
| 70° C., 1 hour | 99 | 63 |
| 80° C., 1 hour | 99 | 60 |
| 90° C., 1 hour | 95 | 53 |
| 100° C., 1 hour | 89 | 43 |
| 100° C., 2 hours | 83 | 35 |

Hereinafter, the fermentation process and the method for preparing the composition of the present invention will be described in detail through examples.

Example 1

Fresh *Allium tuberosum* was purchased at a market as a raw material, trimmed, washed and cut to a size of 2 to 5 cm to prepare 500 g of *Allium tuberosum*. 2.5 L of water, corresponding to an amount of 5 times the weight of the *Allium tuberosum*, was added thereto and sterilized, then yeast for inoculation (MD315) was added in an amount of 0.5% (v/v) of the total volume, and sterilized air was supplied at 0.3 vvm (volume/volume/min) based on the total culture medium volume. The culture was conducted at a constant temperature of 30 degrees Celsius for 70 hours. The pH, at which fermentation was completed, was 7.9. The fermentation broth was filtered to remove the *Allium tuberosum* leaves and thereby to obtain 2.45 L of the fermentation broth. At this time, the concentration of nitrite ions was 345 ppm. An extract having an anthocyanin content of 2% (w/w) as a purple corn extract was prepared using 200 ml of the fermentation broth, was added in an amount of 6.9 g, which corresponds to 690 ppm, to adjust the ratio of anthocyanin to nitrite ions to 1:2, and then dissolved thoroughly. In order to sterilize the extract, the resulting solution was sterilized at 90° C. for 1 hour and cooled to finally obtain a fermented *Allium tuberosum* containing anthocyanin of the present invention. Finally, the concentration of nitrite ions in the sterilized and fermented *Allium tuberosum* product was 330 ppm, which means that 95% or more of nitrite ions remained compared to the initial fermentation broth.

Example 2

The fermentation broth obtained in Example 1 was dispensed into 11 aliquots of 200 ml each, and a stabilizer was added thereto as follows: 1) no addition, 2) blueberry extract (anthocyanin 0.5% (w/w)), 3) aronia extract (anthocyanin 0.7% (w/w)), 4) *Rubus coreanus* Miguel extract (anthocyanin 1.0% (w/w)), 5) black rice extract (anthocyanin 0.2% (w/w), 6) mulberry extract (anthocyanin 0.8% (w/w)), 7) general corn extract (anthocyanin 0%) 8) black soybean extract (anthocyanin 0.3% (w/w), 9) *Schisandra chinensis* extract (anthocyanin 0.2% (w/w)), 10) Vitamin C, 100 mg, and 11) purple corn extract (anthocyanin 2% (w/w). The resulting mixture was sterilized at 90° C. for 1 hour, the concentration of remaining nitrite ions was analyzed, and the proportion of remaining nitrite ions was calculated. The results are shown in Table 2 below.

TABLE 2

| Proportion of remaining nitrite ions (%) after adding extract to 200 ml of fermentation broth and sterilization | | | | | | | | | | |
|---|---|---|---|---|---|---|---|---|---|---|
| 1) | 2) | 3) | 4) | 5) | 6) | 7) | 8) | 9) | 10) | 11) |
| Amount of extract added (g) 0 | 4 | 4 | 4 | 4 | 4 | 5 | 4 | 4 | 0.1 | 0.00345 |
| Remaining nitrite ion (%) 55 | 88 | 89 | 92 | 76 | 88 | 61 | 78 | 75 | 68 | 66 |

It can be seen that addition of anthocyanin is very effective for minimizing the loss of natural nitrite ions contained in the fermented *Allium tuberosum* product of the present invention during the sterilization process. In addition, 11) the purple corn extract (anthocyanin 2% (w/w) in which a ratio of nitrite ion to purple corn extract is 1:0.05 ml), which is the minimum addition concentration of the present invention, could exhibit somewhat weak, yet a stabilization effect.

INDUSTRIAL AVAILABILITY

The present invention relates to a method for preparing a fermented *Allium tuberosum* product that is capable of stably supplying nitrite ions that can be converted into nitric oxide, which is the most important signal transducer in the cardiovascular system in the body when ingested orally, and a composition for stabilizing the same. The present invention can be applied to foods for recovery, health functional foods, natural medicines and the like and thus can be commercialized in the form of beverages, powders, capsules, tablets and the like.

The invention claimed is:

1. A method for increasing the thermal stability of nitrite ions by anthocyanin in a fermented *Allium tuberosum* composition containing the nitrite ions, the method comprising:
   1) Washing and slicing *Allium tuberosum*, adding water thereto in an amount of 3 to 10 times weight of the *Allium tuberosum*, inoculating a *Saccharomyces cerevisiae* MD315 strain having the accession no. KCTC13835BP for fermentation, and culturing the strain for 2 to 4 days to obtain a fermented *Allium tuberosum* solution containing produced nitrite ions; and
   2) adding anthocyanin to the fermented *Allium tuberosum* solution in a ratio of nitrite ions to anthocyanin of 1:0.001 to 1:2.0, based on the content of nitrite ions contained in the fermented *Allium tuberosum* solution, followed by dissolution,
   wherein the fermented *Allium tuberosum* solution containing produced nitrite ions has 100 to 1,000 ppm of nitrite ions.

* * * * *